United States Patent [19]

Hilaire et al.

[11] Patent Number: 5,545,134

[45] Date of Patent: Aug. 13, 1996

[54] RAPID-EXCHANGE DILATATION CATHETER

[75] Inventors: Pierre Hilaire; Vincent Lagarde, both of Paris, France

[73] Assignee: Laboratoire Nycomed SA, Paris, France

[21] Appl. No.: 330,028

[22] Filed: Oct. 27, 1994

[30] Foreign Application Priority Data

Apr. 15, 1994 [FR] France .................................. 94 04497

[51] Int. Cl.⁶ ................................................. A61M 29/00
[52] U.S. Cl. ........................ 604/96; 604/280; 604/282; 606/194
[58] Field of Search ........................... 604/96, 100, 102, 604/160, 282; 128/772

[56] References Cited

U.S. PATENT DOCUMENTS

| 5,112,304 | 5/1992 | Barlow et al. | 604/96 |
| 5,324,269 | 6/1994 | Miraki | 604/160 |
| 5,338,295 | 8/1994 | Cornelius et al. | 604/96 |
| 5,364,357 | 11/1994 | Aase | 604/96 |
| 5,370,615 | 12/1994 | Johnson | 604/96 |
| 5,382,234 | 1/1995 | Cornelius et al. | 604/96 |

FOREIGN PATENT DOCUMENTS

WO94/04216  8/1993  WIPO ........................ A61M 29/021

*Primary Examiner*—C. Fred Rosenbaum
*Assistant Examiner*—Anh-Tuan T. Nguyen
*Attorney, Agent, or Firm*—James J. Leary

[57] ABSTRACT

The present invention relates to a rapid-exchange dilatation catheter of the type comprising a flexible tubular body having a distal part, an intermediate part and a proximal part.

According to the invention, the body comprises a core having a high modulus of elasticity, which core is permanently joined at one end to the proximal part and embedded at its other end in a wall defining an inner duct for a guide-wire to pass through.

The invention finds a particular application in the treatment of stenoses of blood vessels.

16 Claims, 2 Drawing Sheets

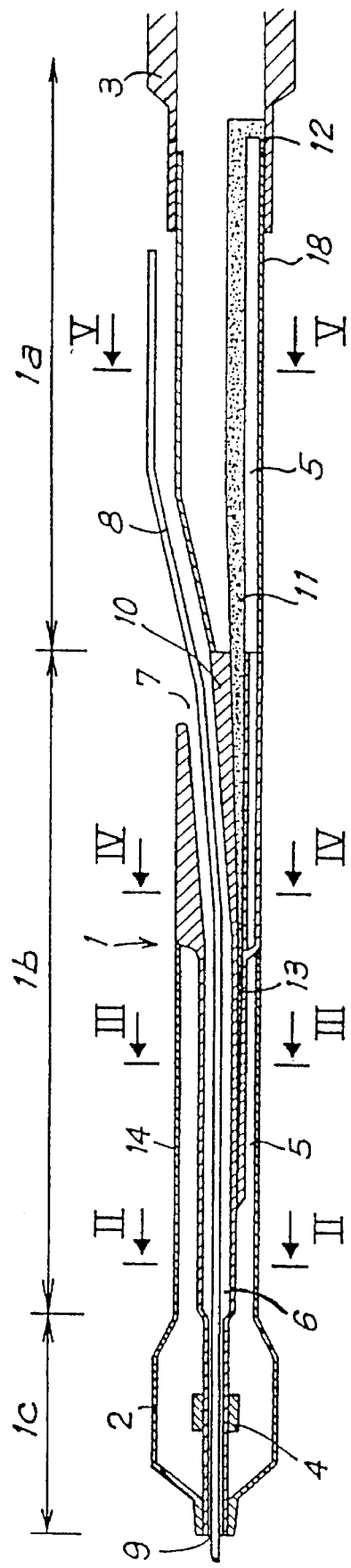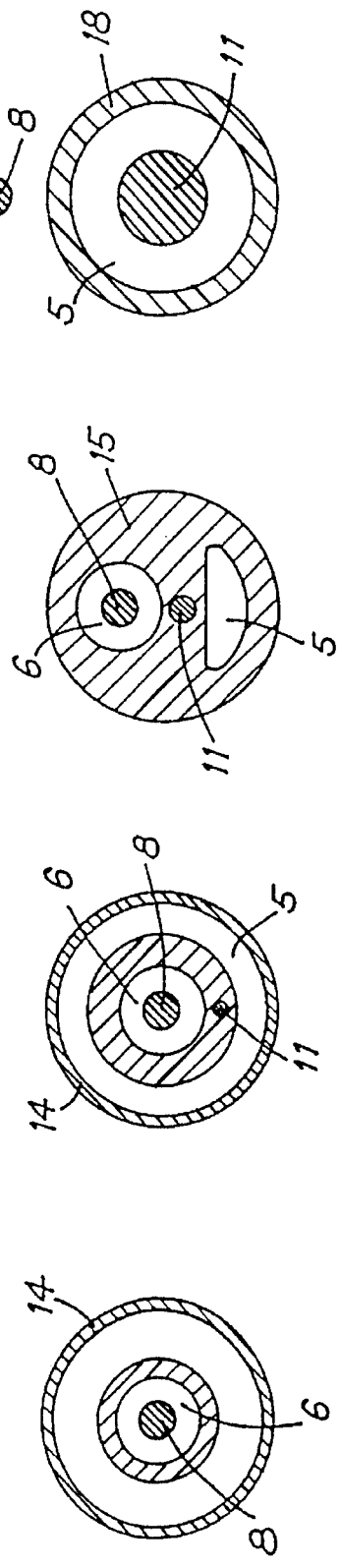

RAPID-EXCHANGE DILATATION CATHETER

FIELD OF THE INVENTION

The present invention relates to a rapid-exchange dilatation catheter, for introduction into a body canal such as for example a blood vessel.

The invention is principally applicable to the treatment of disorders of the coronary arteries but it can also be used for in treating disorders of other body canals, for example the oesophagus or the urethra.

BACKGROUND OF THE INVENTION

Such disorders are generally provoked by the presence, on the inner walls of the canal, of deposits causing strictures or stenoses in said canal.

The treatment of such disorders generally calls for the use of a dilatation catheter for restoring the normal flowing section of the canal at the level of the stenosis by compression with the aid of a balloon.

A guide, nomally produced in the form of a wire is used for helping the catheter to reach the stenosis.

The guide-wire is generally longer than the catheter, say about 20 to 50 cm, in order to urge the catheter forward into the body canal, by sliding it along the wire.

During an operation using the dilatation catheter, it may be necessary, in some cases to change the catheter while leaving the guide-wire in position, for example in case of difficult progression inside the coronaries.

It is known for example from U.S. Pat. No. 4,748,982, incorporated herein by way of reference, to use a so-called "rapid-exchange catheter" of which the distal part comprises two juxtaposed, non-communicating inner ducts, of which one, which is meant for the guide-wire to pass through, issues outside the catheter.

Inasmuch as the guide-wire passes through said catheter only over a small portion of its length, say 20 to 25 cm for a catheter reaching a total length of about 130 cm, said portion being smaller than the length of the wire extending out of the body, i.e. between 35 and 55 cm, it is possible to remove it while keeping said wire in position, and by sliding it along the guide-wire. The initial catheter can thus be replaced with another, without the need to use a specific exchange wire or an extension.

For correctly positioning the balloon at the level of the stenosis, it is necessary to bring the distal end of the catheter to beyond said stenosis.

Understandably, for the catheter to pass through the stenosis, it is generally necessary to apply a thrusting pressure on the latter.

Said thrusting pressure is exerted by the practitioner at the level of the proximal end of the catheter.

Transmission of said thrusting pressure to the distal end of the catheter raises a problem which, heretofore, has not been solved satisfactorily.

SUMMARY OF THE INVENTION

In the circumstances, it is the object of the present invention to solve the technical problem consisting in providing a new design of rapid-exchange dilatation catheter which can be readily produced on an industrial scale, which is easy to use, and which enables an efficient transmission to the distal part comprising the balloon, of the thrusting pressure exerted at the level of the proximal part.

The solution provided by the present invention for solving said technical problem consists in a rapid-exchange dilatation catheter of the type comprising:

a flexible tubular body comprising a distal part, an intermediate part and a proximal part, and having:

a radially deformable portion forming balloon, disposed at the level of its distal part;

a first inner duct issuing at one end inside the balloon, in liquidtight manner, and connected at the other end to a fluid supply source in order to enable inflating and deflating of the balloon;

a second inner duct, which is not communicating with said first inner duct, traversing said distal part and issuing outside said body at the level of the intermediate part and close to the proximal part, said duct being defined by a substantially tubular wall and adapted to allow the passage of a guide-wire, characterized in that said body further comprises a core having a high modulus of elasticity and being permanently joined at one end to the proximal part and embedded at its other end in said wall defining said second inner duct.

The novelty of the present invention therefore resides in the use of an element intended for rigidifying the body of the catheter, and in particular at least part of the wall defining the duct through which passes the guide-wire, and for ensuring a reliable and safe transmission to the distal part, of the thrusting pressure exerted at the level of the proximal part of the catheter.

As the core is embedded in the wall of said second inner duct, there is no noticeable reduction of the flowing section of the fluid used for inflating the balloon. Such configuration therefore does not in any way reduce the balloon inflating and deflating time.

According to a particular characteristic, said core has a cross-section which is decreasing from its proximal end towards its distal end.

The gradual decrease of the cross-section of the core therefore confers to the catheter assembly a progressive flexibility under bending and prevents all risks of breaking or plicature thereof.

The resulting catheter shows relatively high rigidity in its proximal part, and a certain amount of flexibility in its distal part, the passage from the rigid part to the more flexible part being done without any breaking.

In other words, the catheter according to the present invention comprises a sufficiently rigid body to allow a good transmission towards the distal part, of the thrusting pressure exerted on the proximal part while ensuring sufficient flexibility at the level of said distal part to enable easy maneuverability of the catheter particularly in the bent portions of the body canal.

The terms "with high modulus of elasticity" as used within the present description and claims, are meant to cover any materials having a modulus of elasticity of at least 10000 MPa.

Advantageously, said core is produced in a metallic material, preferably steel.

According to another characteristic of the invention, said core extends in the intermediate part up to a point situated upstream and in the immediate vicinity of the balloon-forming portion.

The term upstream as used herein designates the part of the proximal side which is external to the balloon.

Such particular configuration prevents all risks of the balloon being perforated by said core while making sure that the thrusting pressure is transmitted up to the stenosis.

According to a particular embodiment, the flexible tubular body of a catheter according to the invention comprises:
- a proximal part constituted by a hollow tube (18) of which the distal end is slightly flattened;
- a distal part comprising a substantially axial inner duct forming the distal part of said second inner duct and an outer tube surrounding coaxially said inner tube and comprising a radially deformable portion forming balloon;
- an intermediate part forming a liquidtight connection between the proximal and distal parts, comprising an outer tube extending said inner tube of the distal part and being joined at its proximal end to a two-channel tube whose distal part has been stretched in order to form an inner duct extending in liquidtight manner the inner duct of said distal part.

BRIEF DESCRIPTION OF THE DRAWINGS

The invention will be more readily understood, and other characteristics and advantages thereof will emerge from the following description of a currently preferred embodiment of the invention, given with reference to the accompanying drawings, in which:

FIG. 1 is a view of a longitudinal section of a rapid-exchange dilatation catheter according to the present invention, FIG. 2 is a cross-sectional view along line II—II of FIG. 1, FIG. 3 is a cross-sectional view along line III—III of FIG. 1, FIG. 4 is a cross-sectional view along line IV—IV of FIG. 1, FIG. 5 is a cross-sectional view along line V—V of FIG. 1.

DETAILED DESCRIPTION OF A PREFERRED EMBODIMENT

Figure 6:
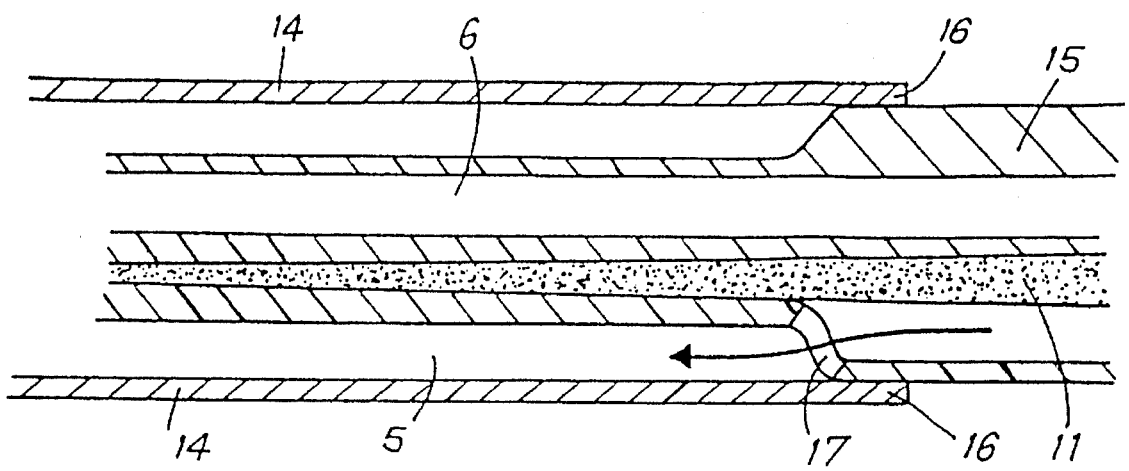
FIG. 6 is a detailed view of a longitudinal section showing the substantially central portion of the intermediate part of a dilatation catheter according to the present invention.

In the following description, the body canal selected by way of example is a blood vessel not shown, such as in particular a coronary artery.

FIG. 1 thus diagrammatically illustrates a rapid-exchange dilatation catheter according to the invention.

Said catheter comprises a flexible tubular body 1 having a proximal part 1a, an intermediate part 1b and a distal part 1c.

By way of example, for a catheter having a total length of 135 cm, the proximal part 1a may have a length of about 111 cm, the intermediate part 1b a length of about 21 cm and the distal part 1c length of about 3 cm.

Preferably, the flexible tubular body 1 has a cross-section which is substantially circular and constant throughout most of its length.

The body 1 is provided at the level of its distal part 1c with a radially deformable portion 2 forming balloon, and at the level of its proximal part 1a, with a connector element 3.

Said connector element 3 is a conventional one-channel element enabling the connection with a fluid supply source to allow inflating and deflating of the balloon 2.

The flexible body 1 may be produced for example from one or more semi-rigid thermoplastic materials selected among the polyethylenes, polyamides or even copolymers of PEBAX® or HYTREL® type.

The radially deformable balloon-forming portion 2 may be integrated to the flexible body 1, such as in the illustrated example, or fixed thereon in liquidtight manner by conventional means such as for example heat-sealing or an adhesive. Said portion may also be produced from a thermoplastic material such as for example a polyamide, a polyethylene or even a polyester.

In the drawings, the balloon-forming portion is shown in inflated state.

For easy positioning of the balloon 2 at the level of the stenosis, i.e. before inflating, the body 1 may be equipped with identification means such as a radiopaque metallic ring 4; such radiopaque ring may be produced in a metal such as gold, platinum, tungstene or alloys thereof.

Generally speaking, the flexible body 1 comprises a first inner duct 5, extending substantially longitudinally, said duct 5 issuing at its distal end into the balloon 2, in liquidtight manner, and being joined at its proximal end, via the connector element 3, to a fluid supply source, not shown, in order to enable inflating and deflating of the balloon 2.

The flexible body 1 further comprises a second inner duct 6, non-communicating with the first inner duct 5, which passes through the distal part 1c, and extends at the level of the intermediate part 1b to issue on the outside of said body via an opening 7 situated downstream of and close to the proximal part 1a.

The second inner duct 6 is defined by a substantially tubular wall to be described hereinafter in more details, and is so adapted as to allow the passage of a guide-wire 8 emerging at the distal end of the catheter via an opening 9 provided to this effect. The guide-wire 8, normally in metal, may be introduced in the catheter by catching its proximal end and threading it forward into the inner duct 6 through the distal opening 9 and up to the proximal end 7.

Advantageously, the wall forming the second inner duct 6 has, at the level of the proximal opening 7, the shape of a ramp intended for guiding the wire 8 out of the catheter.

In the currently preferred embodiment illustrated in FIG. 1, the inner ducts 5 and 6 extend substantially longitudinally inside the body 1 and are coaxial in the intermediate and distal parts, 1b and 1c respectively. The proximal part 1a and distal part 1c are interconnected in liquidtight manner by the intermediate part 1b, as will be explained in more details with reference to FIGS. 6 and 7.

The body 1 further comprises a core 11 having a high modulus of elasticity, which core is permanently joined at one end 12 to the proximal part 1a and embedded at its other end 13 in the wall defining the second inner duct 6 at the level of the intermediate part 1b.

Advantageously, the core 11 is joined to the proximal end of the catheter at the level of the connector element 3, for example by adhesive bonding or sealing thereon.

Preferably, the end 12 of the core is U-bent in order to joint the core 11 to the connector element 3.

The core 11 has a cross-section which is, for example, circular, and which decreases from its proximal end 12 towards its distal end 13.

The distal end 13 is situated in the immediate vicinity and upstream of said balloon-forming portion 2.

Figure 7:
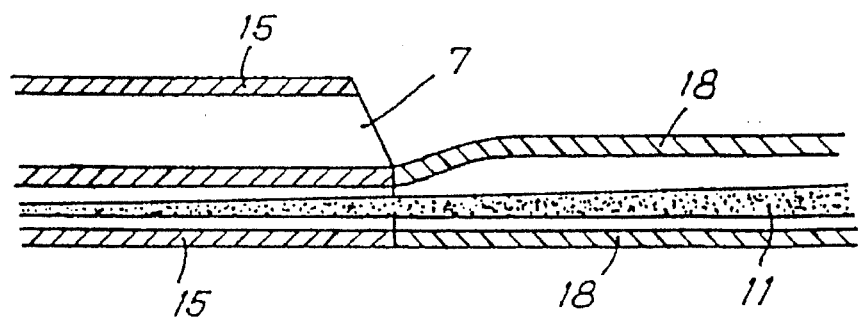
FIG. 7 is a detailed view of a longitudinal section showing the connection between the intermediate and proximal parts of a dilatation catheter according to the invention.

The intermediate part of a dilatation catheter according to the invention is now described in more details with reference to FIGS. 6 and 7.

As can be seen in FIG. 6, the balloon-forming radially deformable wall 2 of the distal part 1c is extended by an outer tube 14 which extends over a portion of the intermediate part 1b.

The second inner duct 6 which is coaxial with respect to the outer tube 14, is obtained by stretching, on the distal side, a multi-channel tube 15, which extends said outer tube 14 on the proximal side.

In the illustrated example, the tube 15 is a two-channel tube.

As shown in FIG. 4, said tube 15 comprises in its upper part a channel with substantially circular cross-section which, once drawn, constitutes the second inner duct 6 for the passage of the guide-wire 8, and in its lower part a second channel with a cross-section having substantially the shape of a crescent or kidney, which progressively disappears by stretching (see FIG. 3).

The metallic core 11 is disposed in the second channel, and understandably, it remains embedded at the level of its distal end in the wall of the tube which constitutes the second inner duct 6 after stretching.

The outer tube 14 is fixed by its proximal end 16 to the two-channel tube 15, preferably by heat-sealing.

An opening 17 is made at the level of the narrowing in the lower part of the two-channel tube 15 so as to constitute a passageway for the fluid intended for inflating and deflating the balloon.

The joint between the intermediate part 1b and the proximal part 1a of a dilatation catheter according to the invention is now described in more details with reference to FIG. 7.

The proximal part 1a is constituted by a hollow tube 18 inside which is disposed the core 11.

To allow connection with said two-channel tube 15, the distal end of tube 18 is slightly flattened in order to constitute a channel whose cross-section is substantially identical to that of said lower channel of the tube 15.

The connection is achieved by placing in contact and sealing the tubes 15 and 18 previously arranged so that the lower channel of the two-channel tube 15 and the channel formed at the previously flattened distal end of tube 18 are placed in register. The resulting connection is liquidtight.

Said opening 7 is formed by cutting out the proximal end of the two-channel tube 15, the flattened upper part of tube 18 constituting said ramp for guiding the wire 8 towards the outside of the catheter.

The operation and use of the rapid-exchange dilatation catheter described hereinabove is in conformity with those described in the prior art to which the man skilled in the art can refer.

In general, a guiding catheter is first introduced in the patient's vessel.

Then, a dilatation catheter according to the present invention, of preselected suitable size and a guide-wire 8 is introduced into said guiding catheter by initially inserting the guide-wire up to the stenosis, and then advancing the catheter until the balloon 2 reaches a position facing the stenosis.

To replace the dilatation catheter with a different one, it suffices to hold the guide-wire in position in the stenosis and to remove the catheter by sliding it along the wire 8.

When the catheter is separated from the guide-wire 8, another catheter can be threaded on the wire 8 and moved forward up to the stenosis.

What is claimed is:

1. A rapid-exchange dilation catheter, for introduction into a body canal such as for example a blood vessel, of the type comprising:

a flexible tubular body comprising a distal part, an intermediate part and a proximal part, and having:

a radially deformable portion forming a balloon, disposed at the level of said distal part;

a first inner duct issuing at one end inside the balloon, in liquidtight manner, and having means at the other end for connecting to a fluid supply source in order to enable inflating and deflating of the balloon;

a second inner duct, which is not communicating with said first inner duct, traversing said distal part and issuing outside said flexible tubular body at the level of the intermediate part and close to the proximal part, said duct being defined by a substantially tubular wall and adapted to allow the passage of a guide-wire, wherein said flexible tubular body further comprises a core having a high modulus of elasticity and being permanently joined at one end to the proximal part and embedded at its other end in said wall defining said second inner duct.

2. The rapid-exchange dilation catheter of claim 1, wherein said core has a cross-section which is decreasing from its proximal end towards its distal end.

3. The rapid-exchange dilation catheter of claim 1, wherein said core is in metal.

4. The rapid-exchange dilation catheter of claim 1, wherein said core extends in the intermediate part up to a point situated upstream and in the immediate vicinity of the balloon-forming portion.

5. The rapid-exchange dilation catheter of claim 1, wherein the second inner duct has, at the level of its end issuing into the catheter, the shape of a ramp intended for guiding the wire out of the catheter.

6. The rapid-exchange dilation catheter of claim 1, wherein:

said proximal part of said flexible tubular body is constituted by a hollow tube having a distal end which is slightly flattened;

said distal part of said flexible tubular body comprises a substantially axial inner tube forming the distal part of said second inner duct and an outer tube coaxially surrounding said inner tube and comprising a radially deformable portion forming said balloon; and said intermediate part of said flexible tubular body forms a liquidtight connection between the proximal and distal parts, said intermediate part comprising an outer tube extending from said outer tube of the distal part and being joined at its proximal end to a two-channel tube whose distal part has been stretched in order to form an inner duct connected in liquidtight manner to the inner tube of said distal part.

7. The rapid-exchange dilation catheter of claim 1, wherein said core has a U-bent proximal end.

8. The rapid-exchange dilation catheter of claim 1, wherein said core is made of steel.

9. A rapid-exchange dilation catheter comprising:

a flexible tubular body having a distal part, an intermediate part and a proximal part;

an expandable dilation balloon mounted on said distal part of said flexible tubular body;

a first inner duct within said flexible tubular body, said first inner duct having a distal end in fluid communication with an interior space of said dilation balloon and a proximal end having means for connecting said first inner duct to a fluid supply source in order to enable inflating and deflating of said dilation balloon;

a second inner duct within said flexible tubular body having a lumen adapted to allow the passage of a guide-wire, said second inner duct traversing said distal part of said flexible tubular body and communicating with a guide-wire port on an exterior surface of said intermediate part of said flexible tubular body, said second inner duct being defined by a substantially tubular wall; and a core having a high modulus of elasticity, said core having a proximal end permanently joined to the proximal part of said flexible tubular body and a distal end embedded in said wall defining said second inner duct.

10. The rapid-exchange dilation catheter of claim 9 wherein said core has a cross section which is decreasing from its proximal end towards its distal end.

11. The rapid-exchange dilation catheter of claim 9 wherein said core is made of metal.

12. The rapid-exchange dilation catheter of claim 9 wherein said distal end of said core extends into the distal part of said flexible tubular body to a point immediately proximal to said dilation balloon.

13. The rapid-exchange dilation catheter of claim 9 wherein said guide-wire port of said second inner duct has the shape of a ramp adapted for guiding the guide-wire out of the catheter.

14. The rapid-exchange dilation catheter of claim 9, wherein:

said proximal part of said flexible tubular body comprises a hollow tube having a distal end which is slightly flattened;

said distal part of said flexible tubular body comprises a substantially axial inner tube forming the distal part of said second inner duct and an outer tube coaxially surrounding said inner tube and comprising a radially deformable portion forming said dilation balloon; and said intermediate part of said flexible tubular body forms a liquidtight connection between the proximal and distal parts, said intermediate part comprising an outer tube extending from said outer tube of the distal part and being joined at its proximal end to a two-channel tube having a distal part having a reduced diameter to form an inner duct connected in liquidtight manner to the inner tube of said distal part.

15. The rapid-exchange dilation catheter of claim 9 wherein said core has a U-bent proximal end.

16. The rapid-exchange dilation catheter of claim 9 wherein said core is made of steel.

\* \* \* \* \*